United States Patent [19]

Rooney et al.

[11] Patent Number: 5,491,263
[45] Date of Patent: Feb. 13, 1996

[54] AMINOETHYLATION PROCESS FOR PRODUCTION OF SUBSTITUTED ETHYLENE DIAMINES

[75] Inventors: Peter C. Rooney; Michael O. Nutt, both of Lake Jackson, Tex.

[73] Assignee: The Dow Chemical Company, Midland, Mich.

[21] Appl. No.: 171,039

[22] Filed: Dec. 21, 1993

[51] Int. Cl.$^6$ .................................................. C07C 211/10
[52] U.S. Cl. ........................ 564/369; 544/401; 544/402; 564/503; 564/506
[58] Field of Search ........................ 544/401, 402; 564/369, 503, 506

[56] References Cited

U.S. PATENT DOCUMENTS

| | | | |
|---|---|---|---|
| H1,401 | 1/1995 | Campbell | 514/63 |
| 4,381,401 | 4/1983 | Poindexter | 556/410 |
| 4,387,249 | 6/1983 | Harnden et al. | 564/488 |
| 4,404,356 | 9/1883 | Andrews et al. | 528/99 |
| 4,444,694 | 4/1984 | Hsieh | 260/513 B |
| 4,578,517 | 8/1986 | Johnson et al. | 564/479 |
| 5,246,619 | 9/1993 | Niswander | 252/183.11 |

OTHER PUBLICATIONS

"The Use of 2-Oxazolidinones as Latent Aziridine Equivalents. 2. Aminoethylation of Aromatic Amines, Phenols, and Thiophenols," Poindexter et al, Journal of Organic Chemistry, pp. 6257–6265 (1993).
"Your Ethyleneamines Resource," The Dow Chemical Company, 1991.
Nakata et al., Tetrahedron Letters, vol. 32, No. 39, pp. 5363–5366 (1991).

*Primary Examiner*—Glennon H. Hollrah
*Assistant Examiner*—Scott C. Rand

[57] ABSTRACT

A process is disclosed for producing a substituted ethylenediamine, the process comprising reacting an oxazolidinone with a secondary amine or an alkanolamine. The process includes, in one aspect, reacting precursors of the oxazolidinone in situ.

11 Claims, No Drawings

AMINOETHYLATION PROCESS FOR PRODUCTION OF SUBSTITUTED ETHYLENE DIAMINES

BACKGROUND OF THE INVENTION

1. Field of the Invention

This invention is directed to aminoethylation processes for producing substituted ethylene diamines; in one aspect, substituted ethylenediamines are produced by reacting oxazolidinones (also called oxazolidones) or their precursors with secondary amines or alkanolamines.

2. Description of Related Art

Prior art methods for producing ethylenediamines employ relatively expensive starting materials and result in a variety of by-products. In one typical prior art process ethylene amines are continuously produced by reacting ammonia with ethylenedichloride. Neutralization with sodium hydroxide follows, producing amines and salt. Salt separation yields a mixture of amines, water and unreacted ammonia. Distillation of the mixture produces a variety of products in the ethyleneamine family, including: ethylenediamine (EDA), diethylenetriamine (DETA), triethylenetetramine (TETA), tetraethylenepentamine (TEPA), pentaethylenehexamine (PEHA), Ethyleneamine E-100, piperazineamine mix, aminoethylpiperazine (AEP), and aminoethylethanolamine (AEEA).

The prior art discloses the reaction of hydrochloric acid with 2-oxazolidinone to produce 2-chloro-ethyleneamine hydrochloride and carbon dioxide. In another known reaction, aziridine and aziridine salts react with hydrochloric acid to produce ethylenediamines (see Scheme 1); however, evidence of toxic and carcinogenic properties of these reagents severely limit their use. In various prior art processes, amines (primary, aliphatic, aromatic) reacted with oxazolidinones to produce substituted ureas.

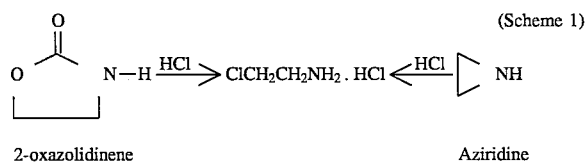

2-oxazolidinene          Aziridine (Scheme 1)

Although electrophiles such as carboxylic and sulfonic acids or carboxylic acid chlorides can undergo decarboxylative ring opening at the C-5 position of 2-oxazolidinone to produce substituted ethylenediamines (see equations 1 and 2), more recent prior art work has shown that aniline salts and thiophenols also produce substituted ethylenediamines. For example, aniline hydrochloride salts reacted with various 2-oxazolidinone to give the ethylenediamines shown in equation 2.

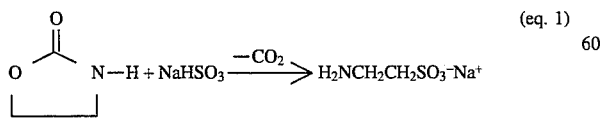

(eq. 1)

No ring opening reaction occurred in the prior art process using either 4,4-dimethyl-2-oxazolidinone (1, below) or 5-ethyl-2-oxazolidinone (2, below) with aniline hydrochloride.

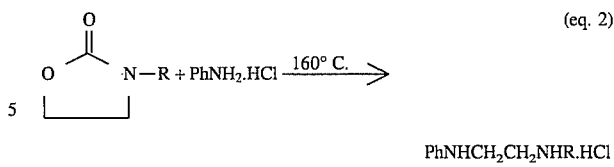

(eq. 2)

PhNHCH$_2$CH$_2$NHR.HCl

R = H, Me, CH$_2$Ph, Ph

It has been shown that the reaction of oxazolidinones with aliphatic or aromatic amines affords N-(2-hydroxyethyl)ureas (3, below) and imidazolidinones (4, below) via attack at the C-2 ring carbonyl position of the oxazolidinone (see equation 3). Imidazolidinones are obtained by dehydration of the urea due to the higher temperatures required for the reaction of aromatic amines with the oxazolidinone.

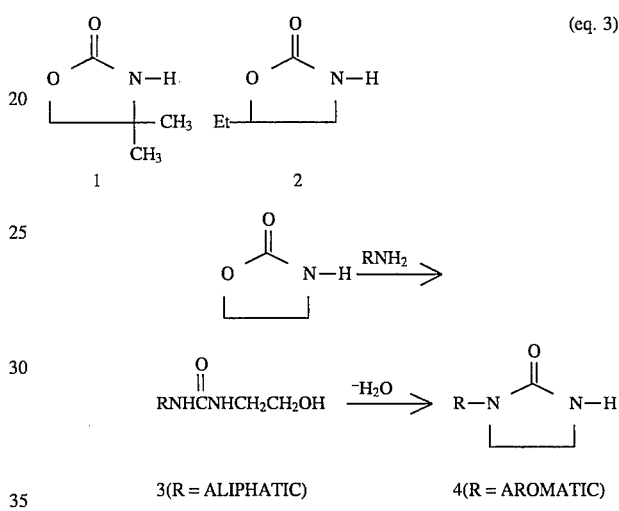

(eq. 3)

3(R = ALIPHATIC)        4(R = AROMATIC)

According to certain prior art, aliphatic amines and hydrochloride salts of aliphatic amines do not ring open oxazolidinones to yield ethylenediamines. For example, the reaction of 2-oxazolidinone with n-BuNH$_2$·HCl in 2-(2-methoxyethoxy)ethanol at 160° C. failed to give any diamine product after 12 hours. Starting amine and oxazolidinone were recovered unchanged. The prior art explanation is that the reluctance of aliphatic amine salts to promote ring opening is due to their being less acidic than aromatic amine salts (pKa's of 5 for aromatic vs. pKa's of 10 for aliphatic amine salts; "pKa" is the pH at the half-neutralization point when the amine is reacted with acid; it is the logarithm of the amine protonation equilibrium reaction constant) and therefore are not strong enough acids to initiate the reaction. The prior art teaches than the degradation of diethanolamine with carbon dioxide is kinetically consistent with an oxazolidinone intermediate mechanism and discloses that N-(2-hydroxyethyl)oxasolidinone (HEOD) is involved in the formation of N,N,N'-tris(2-hydroxyethyl)- ethylenediamine (THEED) when diethanolamine (a secondary alkanolamine) is reacted with HEOD in the presence of carbon dioxide.

SUMMARY OF THE PRESENT INVENTION

The present invention, in one aspect, discloses a process for producing substituted ethylenediamines by reacting oxazolidinones or their precursors with alkanolamines or secondary amines. The substituted ethylenediamines include (but are not limited to) EDA, DETA, TETA, TEPA, PEHA, E-100, and piperazine. The oxazolidinones include (but are not limited to) 3-methyl-2-oxazolidinone, 3-phenyl-2-oxazolidinone, 3-(2-hydroxypropyl-5-methyl-2oxazolidinone), 3-(2-hydroxy ethyl)-2-oxazolidinone and 2-oxazolidone. The alkanolamines include but are not limited to diethanolamine, monomethylethanolamine and diisopropanolamine. The secondary amines include but are not limited to aminoethylpiperazine. In certain embodiments a reaction according to this invention is conducted with an excess of alkanolamine or secondary amine producing ethyleneamine, a secondary alkanolamine, which reacts further to give higher molecular weight ethylenediamines. In certain preferred embodiments the reaction is conducted at a temperature between twenty degrees Centigrade and about two hundred and eighty degrees Centigrade; more preferably between about ninety and about two hundred and ten degrees Centigrade; and most preferably between about one hundred twenty and about one hundred eighty degrees Centigrade.

The ring opening reactions of 2-oxazolidinones with secondary aliphatic alkanolamines or secondary amines proceeds smoothly producing a substituted ethylenediamine derivative. Ethylenediamines ($R^1R^2NCH_2CH_2NHR^3$ where $R^1$=alkyl, $R^2$=alkyl or 2-hydroxyethyl and $R^3$=alkyl or H) are formed in high yields when the oxazolidinone and excess secondary alkanolamine or amine are heated to between about 150 degrees Centigrade and about 225 degrees Centigrade. The reaction appears to be catalyzed by small amounts of hydrochloric acid.

Compared to other methods of producing substituted ethylenediamines, this method, in certain embodiments, uses inexpensive starting materials (especially if precursors such as (but not limited to) urea or dialkylcarbonates are used to generate the oxazolidinone, Preferably in situ) and produces only carbon dioxide as a by-product.

Potential uses of these substituted ethylenediamines include, but are not limited to, acid gas (carbon dioxide and hydrogen sulfide) treating solvents, surfactant intermediates and metal working fluid additives.

In one embodiment the present invention discloses a process for the preparation of 1,2-ethanediamine compounds which includes contacting a 2-oxazolidinone with an aliphatic secondary amine or an aliphatic secondary alkanolamine, under conditions such that a 1,2-ethanediamine is produced; such a process wherein the 2-oxazolidinone corresponds to the formula

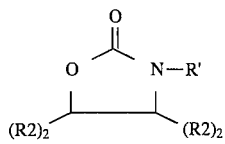

wherein R' is separately in each occurrence hydrogen, C6–20 aryl, C7–20 aralkyl, C1–20 hydrocarbyl or C1–20 hydroxyhydrocarbyl; and $R^2$ is separately in each occurance hydrogen or C1–20 hydrocarbyl; such a process wherein R' is hydrogen, C1–20 alkyl or C1–20 hydroxyalkyl; such a process wherein R' is hydrogen, C1–10 alkyl, C6–20 aryl, C7–20 aralkyl or C1–10 hydroxyalkyl; such a process wherein R' is hydrogen, phenyl, methyl, ethyl or 2-hydroxyethyl; such a process wherein $R^2$ is separately in each occurance hydrogen, C1–20 alkyl, C1–20 alkenyl, C6–20 aryl or C7–20 aralkyl; such a process wherein $R^2$ is hydrogen; such a process wherein the 2-oxazolidinone is 3-methyl-2-oxazolidinone, 3-phenyl-2-oxazolidinone, 3-(2-hydroxypropyl-5-methyl-2-oxazolidinone, 3-2-hydroxyethyl-2-oxazolidinone or 2-oxazolidone, or the like; such a process wherein the aliphatic secondary alkanolamine is diethanolamine, monomethylethanolamine or diisopropanolamine, or the like; and/or such a process wherein the aliphatic secondary amine is of the formula $R^3R^4NH$ wherein $R^3$ and $R^4$ are separately in each occurrence a C1–20 alkyl or C1–20 aralkyl or is a polyethylenepolyamine in which the amine beta to the secondary amine is a tertiary amine such as occurs in aminoethyl-piperazine, or the like.

It is, therefore, an object of at least certain preferred embodiments of the present invention to provide:

New, useful, unique, efficient, nonobvious devices and methods for producing substituted ethylenediamines;

Such processes in which oxazolidinones (or their precursors) are reacted with secondary amines or alkanolamines;

Such processes in which a reaction temperature is maintained between about twenty and about two hundred degrees Centigrade; and most preferably between about one hundred twenty and about one hundred eighty degrees centigrade;

Such processes in which an excess of secondary amine or alkanolamine is used;

Such processes which produce only carbon dioxide as a byproduct; and

Such processes which employ an acid catalyst, e.g. hydrochloric acid.

Certain embodiments of this invention are not limited to any particular individual feature disclosed here, but include combinations of them distinguished from the prior art in their structures and functions. Features of the invention have been broadly described so that the detailed descriptions that follow may be better understood, and in order that the contributions of this invention to the arts may be better appreciated. There are, of course, additional aspects of the invention described below and which may be included in the subject matter of the claims to this invention. Those skilled in the art who have the benefit of this invention, its teachings, and suggestions will appreciate that the conceptions of this disclosure may be used as a creative basis for designing other structures, methods and systems for carrying out and practicing the present invention. The claims of this invention should be read to include any legally equivalent devices or methods which do not depart from the spirit and scope of the present invention.

The present invention recognizes and addresses the previously mentioned problems and long-felt needs and provides a solution to those problems and a satisfactory meeting of those needs in its various possible embodiments and equivalents thereof. To one of skill in this art who has the benefits of this invention's realizations, teachings, disclosures, and suggestions, other purposes and advantages will be appreciated from the following description of preferred embodiments, given for the purpose of disclosure, when taken in conjunction with the accompanying drawings. The detail in these descriptions is not intended to thwart this patent's object to claim this invention no matter how others may later disguise it by variations in form or additions of further improvements.

DESCRIPTION OF EMBODIMENTS PREFERRED

AT THE TIME OF FILING FOR THIS PATENT

Gas chromatography analyses were performed on a HP5890 gas chromatography (upgraded to a Series II) equipped with dual thermal conductivity (TCD) detectors. The column used was a 15m ×0.53mm ×1.0 um film thick DB-Wax megabore column (J&W Scientific). Flow rate (Helium) was adjusted to 7.5 psi. Injector was 230° C., detector was 250° C. The temperature program used was 60° C. for 0 min.; then ramp at 15° C./min. to 230° C., and hold for 5 min. A HP7673 autosampler was used for the 1 uL injections with a Helium split flow of 200 mL/min. HP ChemStation 3365 software was used for data acquisition and calculations. Mass spectrophotometric analyses were performed using a HP5890 series II gas chromatograph connected to a HP5971 Mass selective Detector. The column used was a 30m ×0.25mm ×0.5 um film thick DB-Wax megabore column (J&W Scientific). Flow rate (Helium) was adjusted to 10 psi. Injector was 230° C. and the transfer line was 240° C. Temperature program used was 60° C. for 1 min.; then ramp at 15° C./min. to 230° C., and hold for 15 min. A HP7673 autosampler was used for the 1 uL injections with a Helium split flow of 100 mL/min. HP-MS ChemStation G1030 software was used for data acquisition and calculations. Samples were analyzed using standards of known purity. Mass spectra of each peak was compared to the Wiley spectral library included with the mass spectroscopy software.

General Method of Preparing Ethylenediamine Derivatives from 2-Oxazolidinone

A general method involved reacting the secondary amine or alkanolamine with the oxazolidinone or in situ generated 2-oxazolidinone ("2-Ox") by reaction of the alkanolamine with urea. The following examples show some of the specific substituted ethyleneamine derivatives produced.

Example 1: Reaction of MMEA with 3-methyl-2-oxazolidinone 15.83g of 3-methyl-2-oxazolidinone (0.1567 moles) and 23.3g monomethylethanolamine (MMEA; 0.3102 moles) were placed in a 50mL 45/50 jointed flask equipped with a nitrogen inlet, mechanical stirrer, water condenser, nitrogen outlet to a mineral bubbler and thermocouple probe connected to a Cole Parmer Versatherm Temperature Controller. The temperature was rapidly (10 min.) brought to 115° C. Carbon dioxide evolution was apparent at this temperature. The solution was then heated to reflux (160° C.) for a total of about 5 hours. Gas chromatography (TCD area counts based on starting 3-methyl-2-oxazolidinone) showed the mixture to contain 67.9% DMH (5), 23.4% trimer (6), 2.7% tetramer (7) and 6.0% 3-methyl-2-oxazolidinone. (See eq. 4 for structures).

Example 2: Reaction of DEA with 3-methyl-2-oxazolidinone 15.16g of 3-methyl-2-oxazolidinone (0.1499 moles) and 62.57g diethanolamine (DEA; 0.595 moles) were placed in a 100mL 45/50 jointed flask equipped with a nitrogen inlet, mechanical stirrer, water condenser, nitrogen outlet to a mineral bubbler and thermocouple probe connected to a Cole Parmer Versatherm Temperature Controller. The temperature was rapidly (15 min.) brought to 90° C. Carbon dioxide evolution was apparent at this temperature. The solution was then heated to 140° C. for a total of about 5 hours. GC (TCD area counts based on starting 3-methyl-2-oxazolidinone) showed the mixture to contain 64.6% of entry 7 (Table 1) and 35.4% entry 11 (Table 1; see Eq. 9 for structures).

Example 3: Reaction of HEOD with MMEA 15.71g of 3-(2-hydroxyethyl)-2-oxazolidinone (HEOD; 0.1567 moles) and 51.49g monomethylethanolamine (MMEA; 0.6855 moles) were placed in a 100mL 45/50 jointed flask equipped with a nitrogen inlet, mechanical stirrer, water condenser, nitrogen outlet to a mineral bubbler and thermocouple probe connected to a Cole Parmer Versatherm Temperature Controller. The temperature was slowly (1.5 hr.) brought to 150° C. Carbon dioxide evolution was apparent at this temperature. The solution was then heated at this temperature for a total of about 3 hours. GC (TCD area counts based on starting HEOD) showed the mixture to contain 97.9% N,N' bis(2-hydroxyethyl)-N-methyl ethylenediamine (Entry 8, Table 1; see Eq. 8 for structures).

Example 4: Preparation of Tris (2-hydroxyethyl) ethylenediamine (THEED)

12.4g of 3-(2-hydroxyethyl)-2-oxazolidinone (HEOD; 0.0947 moles) and 51.1g diethanolamine (DEA; 0.487 moles) were placed in a 100mL 45/50 jointed flask equipped with a nitrogen inlet, mechanical stirrer, water condenser, nitrogen outlet to a mineral bubbler and thermocouple probe connected to a Cole Parmer Versatherm Temperature Controller. The temperature was rapidly (0.5 hr.) brought to 150° C. Carbon dioxide evolution was apparent at this temperature. The solution was then heated to 200° C. for a total of about 1.5 hours. GC (TCD area counts based on starting HEOD) showed the mixture to contain 94.8% THEED, 3.6% bis (2hydroxyethyl) piperazine (BHEP) and 1.6% starting HEOD (See Eq. 10 for structures).

Example 5: Reaction of MEA & Urea with Aminoethylpiperazine

The reaction of aminoethylpiperazine (AEP; 232 mmoles, (232 millimoles) with monoethanolamine (MEA; 58 mmoles) and urea (58 mmoles) was performed at 150° C. for 1 hr. and then at 175° C. for an additional hour to remove ammonia with a small nitrogen purge. The mixture was cooled and ammonium chloride acid was added (about 2 mmoles) to catalyze the reaction of the 2-oxazolidinone formed in situ (see equation 9) and the reaction was heated to 225° C. for 5 hours. Analysis of the product showed about 60% bis(aminoethylpiperazine) along with several cyclic ureas. (See Eq. 11 below for structures).

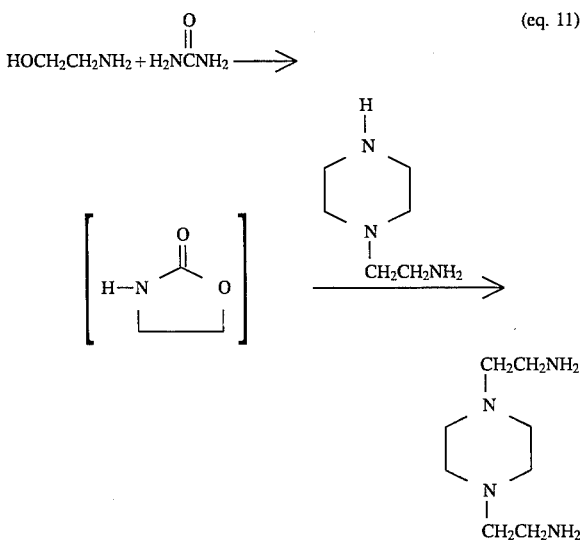

Reaction of MMEA with 3-methyl-2-oxazolidinone (Eg. 1, above)

The reaction of monomethylethanolamine (MMEA) with 3-methyl-2-oxazolidinone produces N,N'-dimethyl-N-(2hydroxyethyl)ethylenediamine (DMH; 5), DMH trimer (6) and DMH tetramer (7) as shown in equation 4.

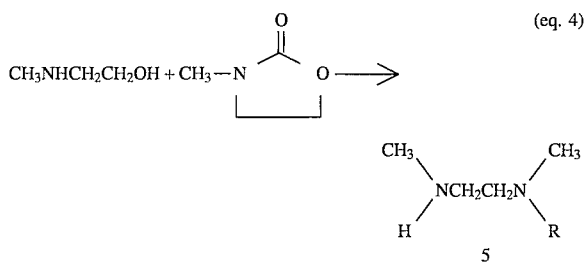

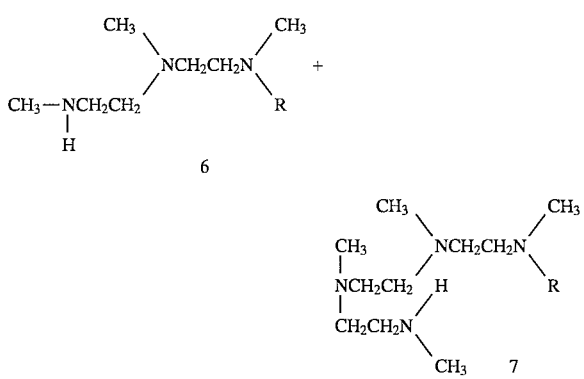

R = CH₂CH₂OH

Gas chromatographic ("GC") and chromatographic/Mass spectroscopy ("GC/MS") retention times of each component are shown in Table 1. Gas chromatographic/mass spectroscopy (EI) (electron impact) of each compound and GC/MS (chemical ionization, using isobutane) of DMH (5), DMH trimer (6) and DMH tetramet (7) confirmed each structure. When a 2:1 mole ratio of MMEA:3-methyl-2-oxazolidinone was heated, initial carbon dioxide evolution was noted at 115° C. Reflux (160° C.) of the solution for 5 hours produced 67.9% DMH, 23.4% trimer, 2.7% tetramer and 6.0% 3-methyl-2-oxazolidinone (GC yield using area counts by thermal conductivity based on starting oxazolidinone). When a 5:1 mole ratio of MMEA to 3-methyl-2-oxazolidinone was refluxed using 0.1g ammonium chloride, 780ppm parts per million chloride as catalyst, it was observed that some carbon dioxide evolution occurred at 60° C. and that vigorous carbon dioxide evolution occurred at 120° C. At 90° C., the amount of DMH detected was 7.8 wt. %. After heating at 140° C. for 2.5 hours, the final sample contained 84.9% DMH, 7.8% trimer, 0% tetramer and 7.3% 3-methyl-2-oxazolidinone. Without being bound to any particular theory or explanation, it appears that hydrochloric acid catalyzes the reaction apparently by protonation of the carbonyl oxygen in the oxazolidinone. This makes it more readily attacked by the amine nucleophile.

| Entry # | Compound | GC[a] | GC/MS[a] |
| --- | --- | --- | --- |
| 1 | Monomethyl ethanolamine (MMEA) | 1.8 | 6.6 |
| 2 | N,N'-dimethyl-N-(2 hydroxyethyl) ethylenediamine (DMH) | 4.5 | 10.2 |
| 3 | 3-methyl-2-oxazolidinone | 6.8 | 12.7 |
| 4 | DMH trimer | 6.9 | 13.2 |
| 5 | Diethanolamine (DEA) | 7.9 | 13.8 |
| 6 | DMH tetramer | 9.4 | 17.0 |
| 7 | DEA + 3-Me-2-Ox reaction product (dimer) | 9.4 | 17.0 |
| 8 | MMEA + HEOD reaction product | 9.5 | 17.0 |
| 9 | 2-Oxazolidone (2-Ox) | 9.8 | 18.0 |
| 10 | Bis-hydroxyethyl piperazine (BHEP) | 9.9 | 18.5 |
| 11 | DEA + 3-Me-2-Ox reaction product (trimer) | 11.1 | 23.4 |
| 12 | Hydroxyethyl-2- oxazolidinone (HEOD) | 11.9 | 26.0 |
| 13 | Tris (2-hydroxyethyl) ethylenediamine (THEED) | 15.5 | 46.6 |

[a]Retention time in minutes

Example 6: Reaction of MMEA with Urea to Make DMH

A one-pot synthesis of DMH was performed using 10.79g urea (0.1792 moles) and 80.94g MMEA (1.078 moles) and heating this mixture for about 2.5 hours. It was expected that urea would react with MMEA to form the oxazolidinone in situ and that further heating would generate DMH in one pot (see equation 5). It was observed that vigorous carbon dioxide gas evolution did occur at 100° C. and that 3-methyl-2-oxazolidinone and DMH were formed by GC analysis. The final product contained 34.5% DMH by GC based on starting urea. The reaction of beta-aminoalcohols with phosgene, dialkyl carbonates, urea, carbon monoxide and carbon dioxide, both with antimony catalyst and without catalyst are well known methods of producing 2-oxazolidinones.

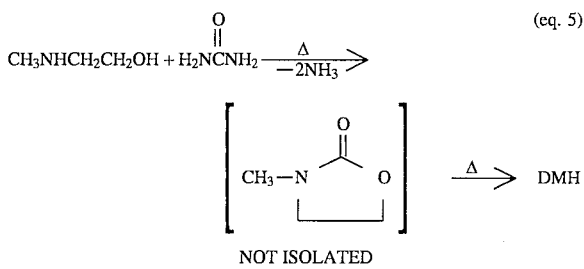

NOT ISOLATED

Known methods for producing DMH

DMH was prepared in 44% yield from MMEA and 2-chloroethylmethylamine hydrochloride (see equation 6) or from N,N-dimethylethylenediamine and ethylene oxide in 68% yield (see equation 7).

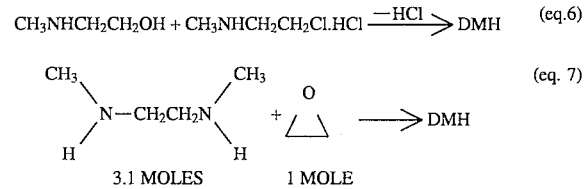

Reaction of MMEA and HEOD (Eg. 3, above)

The reaction of MMEA and 3-(2-hydroxyethyl)-2-oxazolidinone (HEOD) proceeded smoothly and resulted in a 97.9% GC yield (based on starting HEOD) as shown in equation 8. Carbon dioxide evolution was apparent at 150°

C. GC and GC/MS retention times of known purity standards of starting materials and product are shown in Table 1. GC/MS of the product confirmed the structure of the product as N,N'-bis (2-hydroxyethyl )-N-methyl-ethylenediamine.

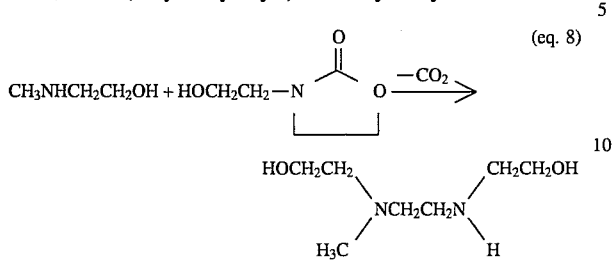

Reaction of DEA with 3-methyl-2-oxazolidinone (Eg. 2, above)

The reaction of diethanolamine (DEA; 0.60 moles) with 3-methyl-2-oxazolidinone (0.15 moles) gave dimer and trimer addition products in almost 2:1 GC ratio with complete conversion (by GC) of the starting oxazolidinone (see equation 9). Vigorous carbon dioxide evolution was observed at 125° C. The reaction was complete in 5 hours total. GC/MS of the dimer and trimer confirmed the structures shown in equation 10.

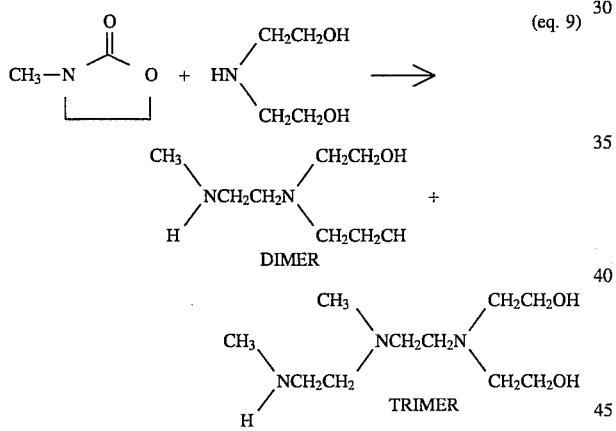

Reaction of DEA with HEOD (Eg. 4, above)

The reaction of DEA with HEOD proceeded smoothly to give N,N,N'-tris(2-hydroxyethyl)ethylenediamine (THEED) and a small amount of bis(2-hydroxyethyl)-piperazine (BHEP; see equation 10). Vigorous carbon dioxide evolution was observed at 140° C. The reaction was complete in about 2 hours total. GC/MS of BHEP was made by comparison with BHEP obtained from a commercial source and THEED was confirmed by GC/MS spectra as well as by comparison to known GC/MS spectra.

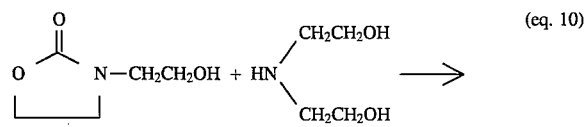

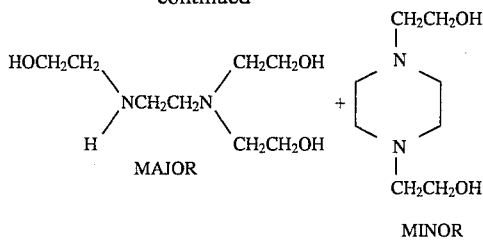

Example 7: Reaction of 3-Phenyl-2-oxazolidinone with MMEA 10.0g of 3-phenyl-2-oxazolidinone (61.3 mmoles) and 55.0g monomethylethanolamine (MMEA;732.3 mmoles) were placed in a 100 ml. reaction flask equipped with a nitrogen inlet, mechanical stirrer, water condenser, nitrogen outlet connected to a mineral bubbler, and thermocouple connected to a Cole Parmer Versatherm Temperature controller. The temperature was quickly raised to 155° C. (30 minutes) and the reaction was stirred at this temperature for 3.5 hours. The final mixture contained 97.6% (by GC) of N-methyl-N-(2-hydroxyethyl)-N-phenyl-ethylenediamine. GC/MS using chemical ionization (isobutane) confirmed the structure to be the ethylenediamine above.

Example 8: Reaction of 3-(2-hydroxypropyl-5-methyl-2-oxazolidinone with MMEA 20.0g of 3-(2-hydroxypropyl-5-methyl-2-oxazolidinone (125.8 mmoles) and 50.1g monomethylethanolamine (MMEA; 667 mmoles) were placed in a 100 ml reaction flask equipped with a nitrogen inlet, mechanical stirrer, water condenser, nitrogen outlet connected to a mineral bubbler, and thermocouple connected to a Cole Parmer Versatherm Temperature Controller. The temperature was quickly raised to 165° C. (30 minutes) and the reaction was stirred at this temperature for 10 hours. The final mixture contained 0.67 weight% (by GC) of N-methyl-N-(2-hydroxyethyl)-N-(2-hydroxypropyl)ethylenediamine. GC/MS using chemical ionization (isobutane) confirmed the structure to be the ethylenediamine above (Formula Weight= 190). Ammonium chloride (0.12g, 2.2 mmoles) was added and the reaction was stirred at 165° C. for an additional 43.5 hours. The final mixture contained 6.8 weight % (by GC) of N-methyl-N-(2-hydroxyethyl)-N-(2 -hydroxypropyl)-ethylenediamine.

In conclusion, therefore, it is seen that the present invention and the embodiments disclosed herein and those covered by the appended claims are well adapted to carry out the objectives and obtain the ends set forth. Certain changes can be made in the subject matter described, shown and claimed without departing from the spirit and the scope of this invention. It is realized that changes are possible within the scope of this invention and it is further intended that each element or step recited in any of the following claims is to be understood as referring to all equivalent elements or steps. The following claims are intended to cover the invention as broadly as legally possible in whatever form its principles may be utilized.

What is claimed is:

1. A process for preparing a 1,2-ethanediamine in a ring opening reaction of an oxazolidinone, the process comprising contacting an oxazolidinone with an aliphatic secondary amine or an aliphatic secondary alkanolamine to effect reaction of the oxazolidinone with the aliphatic secondary amine or aliphatic secondary alkanolamine for a sufficient time to form a 1,2-ethanediamine.

2. The process of claim 1 wherein the oxazolidinone is a 2-oxazolidinone corresponding to the formula

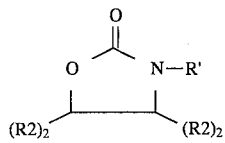

wherein R' is selected from the group consisting of hydrogen, C1–20 hydrocarbyl, C6–20 aryl, C6–20 aralkyl, C1–20 hydroxyhydrocarbyl, C6–20 aralkyl, C1–20 alkyl, C1–20 hydroxyalkyl, C1–10 alkyl, C1–10 hydroxyalkyl, phenyl, methyl, ethyl, and 2-hydroxyethyl and $R^2$ is selected from the group consisting of hydrogen, C1–20 alkyl, C1–20 alkenyl, C6–20 aryl, C6–20 aralkyl, and C1–20 hydrocarbyl.

3. The process of claim 2 wherein the 2-oxazolidinone is selected from the group consisting of 3-methyl-2-oxazolidinone, 3-phenyl-2-oxazolidinone, 3-(2-hydroxypropyl-5-methyl-2-oxazolidinone), 3-(2-hydroxyethyl)-2-oxazolidinone and 2-oxazolidone, and mixtures thereof.

4. The process of claim 1 wherein the aliphatic secondary alkanolamine is diethanolamine, monomethylethanolamine or diisopropanolamine.

5. The process of claim 1 wherein the aliphatic secondary amine is of the formula $R^3R^4NH$ wherein $R^3$ and $R^4$ are a C1–20 alkyl or C1–20 aralkyl.

6. The process in claim 1 wherein the process is conducted at a temperature between about 20° C. and 280° C.

7. The process in claim 1 wherein the process is conducted at a temperature between about 90° C. and 210° C.

8. The process in claim 1 wherein the process is conducted at a temperature between about 120° C. and 180° C.

9. The process of claim 1 wherein an excess of a secondary amine or of a secondary alkanolamine is provided for the process.

10. The process of claim 1 further comprising reacting precursors of the oxazolidinone to produce the oxazolidinone, then reacting the oxazolidinone with the secondary amine or the alkanolamine.

11. The process of claim 10 wherein the precursors are reacted in situ.

* * * * *